United States Patent
Smith et al.

(10) Patent No.: US 7,850,882 B2
(45) Date of Patent: Dec. 14, 2010

(54) PROCESS FOR MAKING INTEGRATED LAYERED URETHANE PRODUCTS

(75) Inventors: James A. Smith, Chatham, MA (US); George Kellett, Cranford, NJ (US)

(73) Assignee: Eveready Battery Company, Inc., St. Louis, MO (US)

( * ) Notice: Subject to any disclaimer, the term of this patent is extended or adjusted under 35 U.S.C. 154(b) by 129 days.

(21) Appl. No.: 12/393,297

(22) Filed: Feb. 26, 2009

(65) Prior Publication Data

US 2009/0212454 A1  Aug. 27, 2009

Related U.S. Application Data

(60) Provisional application No. 61/031,401, filed on Feb. 26, 2008.

(51) Int. Cl.
*B29C 44/24* (2006.01)
(52) U.S. Cl. .................. 264/45.8; 264/45.1; 264/48
(58) Field of Classification Search ............ 264/45.1, 264/45.8, 48
See application file for complete search history.

(56) References Cited

U.S. PATENT DOCUMENTS

| | | | |
|---|---|---|---|
| 6,547,643 B1 * | 4/2003 | Miller et al. ............... 451/28 |
| 6,688,957 B2 * | 2/2004 | Tolles ....................... 451/532 |
| 6,846,480 B2 * | 1/2005 | Smith et al. ............... 424/70.1 |
| 7,332,224 B2 * | 2/2008 | Smith et al. .............. 428/423.1 |
| 7,629,043 B2 * | 12/2009 | Lindsay et al. ........... 428/316.6 |
| 2009/0010983 A1 * | 1/2009 | Melvik et al. ............. 424/422 |
| 2010/0143652 A1 * | 6/2010 | Stockton et al. ............ 428/141 |

* cited by examiner

*Primary Examiner*—Kat Wyrozebski
*Assistant Examiner*—Robert J Grun
(74) *Attorney, Agent, or Firm*—Energizer Personal Care, LLC

(57) ABSTRACT

Polyurethane shapes containing a core layer of a water soluble polymer such as polyethylene oxide (PEO) are produced by casting onto a surface an aqueous mixture containing a pre-polymer of a hydrophilic polyurethane as a first layer of uncured polyurethane, covering the uncured first layer with release paper and compressing the layer, uncovering the uncured first layer and distributing PEO on the uncured surface, applying a second layer of uncured polyurethane on top of the PEO while the polyurethane is still uncured, then covering the resulting mass with release paper and compressing it to form an integrated, layered shaped article containing a core region enriched in PEO that when wetted releases PEO over an extended period. The second layer is applied by adhering about one-half of the first uncured foam layer to the release paper as the first uncured layer is uncovered and then recombining the adhered material on top of the PEO and further compressing the resulting mass to produce an integrated, layered shaped article. The second layer can be applied, alternatively, by independently casting a second layer of uncured polyurethane foam after distributing the PEO and then compressing and curing. The PEO containing shapes are useful in making improved comfort strips for wet shaving razors. Shape products of the process where the core region contains other specified working ingredients are useful in applications including bandages and wound dressings, cosmetic sponges, cleaning and polishing sponges, dry cleaning and anti-static sheets, and in household, industrial and environmental clean up and waste recovery.

8 Claims, 3 Drawing Sheets

PROCESS FOR MAKING INTEGRATED LAYERED URETHANE PRODUCTS

CROSS-REFERENCE TO RELATED APPLICATIONS

This application hereby claims priority to U.S. Provisional Application No. 61/031,401, filed on Feb. 26, 2008.

FIELD OF THE INVENTION

This invention relates to the production of cured, integrated, layered, and water insoluble, hydrophilic polyurethane foam shapes containing a central layer or region enriched in a pre-measured amount of water soluble polymer such as polyethylene oxide or other working ingredient that is released from the polyurethane matrix over an extended period of time or that functions as an absorbent when the urethane foam is exposed to a solvent ingredient such as water. The product is useful in making comfort strips for safety razors, bandages and wound dressings, cosmetic sponges, cleansing and polishing sponges, absorbent sponges for waste or household cleanup and a variety of other applications depending on the properties of the polyurethane layers and the working ingredients.

BACKGROUND OF THE INVENTION

The preparation of hydrophilic urethane foams is known in the art including the preparation of such urethane foams for use in a wide variety of applications in personal care, cleaning and related fields. It is known from the published literature to incorporate a variety of ingredients including cosmetics, cleaning ingredients, vitamins, and the like into urethane pre-polymer mixtures before such mixtures are reacted or blown and cured into sponges that can be employed for a variety of applications. The art also describes post-addition of additives to urethane foams in an effort to load the urethanes with desired ingredients. Such techniques have found application in various products, however, significant problems remain with the use of both pre- and post addition methods for certain applications. There is a need for improvement in the production of comfort strips used in wet shaving razors to produce extended life products that satisfy desired product quality. Additionally, there is a need for more efficient and flexible processing methods to produce shaped polyurethane foam products that are useful for a variety of personal care, cosmetics, cleaning and polishing, and household, industrial and environmental clean up applications.

DISCLOSURE OF THE INVENTION

In its most general aspect, the present invention comprises a method of making layered integrated shaped products of dimensionally stable hydrophilic polyurethane foam or foams containing an internal layer or core region enriched in a working ingredient that is integrated into the foam before it is cured and that is released through the pores of the foam when contacted with a solvent such as a water or, alternatively, containing an absorbent that is integrated into the foam before it is cured and that absorbs or takes up through the pores of the foam liquids such as water or oils with which the foam is contacted. In its most general aspect the shaped products can be made of the same polyurethane foam produced from the same pre-polymer mixture or can be made of two or more foams made from different pre-polymer mixtures and formulations.

In one preferred aspect, the invention comprises a method of making layered shaped integrated products of dimensionally stable hydrophilic polyurethane foam containing an internal layer or core region enriched in a water soluble polymer such as PEO that is integrated into the hydrophilic polyurethane before it has fully cured and that releases over time when exposed to water. Such integrated, layered and shaped product is useful as an improved skin engaging member or comfort strip in a wet shave safety razor having extended life over many successive wettings. Depending on the working ingredient distributed between layers of uncured polyurethane and the properties of the layers of polyurethane, the resulting layered integrated and shaped products are also useful in making bandages wound dressings, cosmetic sponges including those for hair care, facial and body care and make-up application and removal, cleaning and polishing sponges, sponges for home dry cleaning and antistatic applications, absorbent sponges for waste spills in the environment or for industrial and household cleanup. When the working ingredient is a water soluble polymer such as polyethylene oxide or cosmetic or cleaning ingredients the process of the present invention provides a layered integrated polyurethane product that exhibits extended and controlled release of the working ingredient when exposed to water or other solvents.

Novel layered integrated and shaped products of dimensionally stable hydrophilic polyurethane are preferably produced by a process as follows:

a) casting onto a surface an aqueous reaction mixture containing a hydrophilic urethane pre-polymer to produce a dimensionally stable urethane foam when cured thereby producing a first layer of uncured polyurethane foam, and compressing the uncured foam;

b) distributing a composition containing a working ingredient that releases over time when exposed to a solvent or an absorbent onto said first layer of uncured polyurethane foam;

c) thereafter further adding a second layer of uncured polyurethane foam on said first layer and compressing the resulting uncured layered mass, d) curing the layered mass thereby producing a layered integrated and shaped product of dimensionally stable hydrophilic polyurethane containing an integrated internal region enriched in said working ingredient that is an absorbent or that releases over time when exposed to a solvent.

The term "casting" as employed herein is intended to encompass any method whereby a mixture of a suitable urethane pre-polymer containing free isocyanate groups and an aqueous phase preferably containing a surfactant and in certain preferred embodiments a dimensional control ingredient is distributed, flowed, or deposited onto a surface or into a mold where it is permitted to cure and take a desired shape. Casting may take place by gravity, flowing or spraying under ambient or elevated pressure.

The term "dimensionally stable" is intended to cover both rigid and highly pliable or soft polyurethane foams having a porous or open cell structure that permits flow of fluids through the pores or closed cell foams that float on water. As is further described herein a dimensional control ingredient is preferably added to stiffen and make less pliable the resulting foam depending on the ratio of dimensional control ingredient to the selected urethane pre-polymer.

The term "compressing" as employed herein means forceful compression such as takes place when a sheet of material is passed through or under compression rollers or other compression means. Compressing as employed herein also includes containment of an expanding material such as freshly reacting urethane pre-polymers in a closed box so that its shape is altered to take the shape of the box rather than rise and overflow.

While polyethylene oxide (PEO) is a preferred water soluble ingredient for use in making comfort strips from layered, integrated and shaped hydrophilic polyurethanes, other water soluble ingredients can be employed in powdered or particulate form or in fluid form as suspensions or solutions. Suitable water soluble polymers are selected from the group consisting of polyethylene oxide, polyvinyl pyrrolidone, polyacrylamide, hydroxypropyl cellulose, polyvinyl imidazoline, and polyhydroxyethylmethacrylate, and co-polymers and mixtures of said polymers.

Other suitable working ingredients for making layered integrated hydrophilic polyurethane foams and sponges comprise formulations known in the art for making bandages and wound dressings including bioactive ingredients and antibiotics, for cleaning and polishing sponges including formulations of detergents, surfactants and abrasives, cosmetic sponges for personal care applications, dry cleaning and anti-static sheets for use in clothes dryers, and absorbent sponges for household, industrial and environmental cleanup. Such working ingredients are illustrated in examples 6-14, and an array of working ingredients especially suited for cosmetic sponges are described in connection with these examples. Stated another way, suitable other working ingredients are selected from compositions comprising bioactive agents and antibiotics for release from the core layer of wound dressing foams, cosmetic ingredients for release from the core layer of a personal care sponge, detergents or an abrasives for release from the core layer of a cleaning or polishing sponge, dry cleaning and anti static agents for release from sheet or sponge for use in a clothes dryer, and absorbents to take up fluids through the pores of a waste cleanup sponge.

In the practice of the present invention, it has been found that distributing the water soluble ingredient such as PEO directly onto uncured polyurethane is important to achieving effective loading of such ingredient into the layered product for extended life and for achieving satisfactory qualities of the final comfort strip especially in terms of friction reduction.

A water soluble polymer such as PEO and like working ingredients are distributed onto the uncured polyurethane either in liquid or particulate form. The use of slurries is also within the present invention. Other working ingredients that are released over time from the integrated layered product in the presence of solvents also are distributed onto the uncured polyurethane in liquid, particulate or slurry form. Likewise, suitable absorbents are distributed as solids or liquids directly onto the uncured polyurethane.

The term "distributed" is intended to encompass any method of adding the working ingredient directly to the uncured polyurethane to provide a layer or region of such ingredient that is at least partly incorporated into the uncured polyurethane by the mixing action of the ongoing curing reaction, compression and gravitational forces. The distributing of encapsulated working ingredients and polymers which dissolve or absorb over extended periods of time is within the present invention.

When water soluble polymers or like ingredients are employed in powdered or particulate form a preferred particle size range is between about is between about 10 to about 300 mesh and a most preferred range is between about 40 to about 100 mesh (standard screen size.

The water soluble polymer or working ingredient is distributed directly onto the surface of the uncured or partly cured polyurethane in a pre-measured amount based on the designed properties and intended use of the integrated layered and shaped product. In a preferred embodiment about 20 to about 80 weight percent of the final integrated layered product comprises PEO. This range also applies to other water soluble polymers and working ingredients. The pre-measuring of the amount can take place once as a production line is set up or measuring equipment can be installed to measure continuously or batch-wise so that a known amount of working ingredient can be distributed on the uncured foam. The use of roughly estimated quantities is also within the meaning of "pre-measured" amounts.

The term uncured is intended to include polyurethane polymers following casting onto a surface at any stage of curing but does not include fully cured polyurethanes. It is important to distribute PEO or other working ingredient onto the polyurethane and then place the second polyurethane layer before either polyurethane layer is fully cured, and most preferably while in the very early stages of curing so that the mixing action of the curing reaction in conjunction with compression and gravity results in at integration of a part of the PEO or other working ingredient into the uncured polyurethane layers. While not bound by theory or mechanism, such integration results in effective entrapping and then extended release of the PEO or other working ingredients when exposed to water or other solvent. While the period of time for curing of hydrophilic polyurethane pre-polymer mixtures following mixing with the aqueous phase varies considerably depending on the specific formulation and pre-polymers selected and temperature, it is preferred that distributing of PEO or other working ingredient takes place within about two minutes, more preferably within about thirty seconds, and most preferably within about ten seconds of casting the first polyurethane layer.

The process of the present invention permits use of a wide range of hydrophilic urethane pre-polymers containing free isocyanate groups that are capable of making dimensionally stable foams when combined with an aqueous phase. When making more rigid layered integrated foams, the aqueous phase preferably contains a dimensional control ingredient such as wollastonite, a calcium metasilicate of known composition, synthetic variations of wollastonite or other suitable inorganic or organic ingredients, and additionally, preferably, a suitable surface active ingredient.

Suitable dimensional control agents for use in the present invention in addition to wollastonite include syloids (silica and silica gels), talcs, waxes including polyethylenes and natural and synthetic types, Cab-o-sil, silicon dioxide, fumed silica, polysaccharides, sugars, carboxymethylcellulose (CMC), feldspars, silicates of aluminum containing sodium, potassium, iron, calcium, and barium or combinations of these elements, carbonates, sodium carbonate and bicarbonates, sulfates, sodium and potassium sulfates, micro powders and waxes, micro-fibers, "short stuff", cut synthetic fibers, carbon blacks, metal oxides, titanium dioxide and other colored metal oxides.

In accordance with one aspect of the present invention, it is important to control the ratio of urethane pre-polymer to the dimensional control agent in the aqueous phase in order to produce layered integrated products of the desired firmness or softness and the desired rate of release of encapsulated or integrated PEO and the like or other working ingredients according to the planned end use of the resulting layered integrated and shaped polyurethane foam. Preferably the ratio by weight of urethane pre-polymer to dimensional control agent is about 1:2 to about 2:1, and more preferably between about 1.5:2 to about 2:1.5. In accordance with another aspect of the present invention, the desired firmness or softness of the polyurethane foam product can be controlled by the selection of the urethane pre-polymer. The use of no dimensional control ingredient in certain applications where very soft foams are required is within the present invention.

The methods of the present invention permit the use of a wider range of hydrophilic urethane pre-polymers as long as they produce a foam of the desired dimensional stability and degree of affinity for water. One group of preferred polymers are Hypols JM 5002, 3000, and 2002 offered by Dow Chemical Company. Urethane prepolymer compositions suitable for producing the foam pads of the invention are described, for example, in U.S. Pat. Nos. 3,903,232 and 4,137,200. Corresponding commercial products came from the Hypol® product line of W. R. Grace & Co., Lexington. MA, e.g., Hypol® FHP 5000, Hypol® FHP 4000, Hypol® FHP 3000, Hypol® FHP 2000, Hypol® FHP 2000 HD, Hypol® FHP 2002. Hypol® 2000. Hypol® 2002. Hypol® 3000, Hypol® X6100 and Hypol® Hydrogel, now offered by Dow Chemical Company. The liquid resins are produced by reacting polyols of low molecular weight and 3-8 hydroxyl groups with aromatic or aliphatic diisocyanates. After the reaction, the resins have at least two free isocyanate groups per molecule of polyol used. Examples of suitable diisocyanates are toluene diisocyanate, methylene diphenyl isocyanate and isophorone diisocyanate. Other suitable commercial products come from the Aquapol® product line of Freeman Chemical Corporation and the Trepol® product line of Rynel Inc.

In the practice of the present invention, the urethane pre-polymer is brought into contact with an aqueous phase in the mixing zone where the free isocyanate groups of the urethane pre-polymer hydrolyze with evolution of carbon dioxide. This results in the production of an uncured mass of uncured polymer for casting onto a surface where it continues to react and cures over time to a polyurethane foam of the desired shape and pore size.

It is most preferred that the aqueous phase contains a surfactant. Suitable surfactants are selected from among anionic, cationic, dipolar-ionic (zwitterionic), ampholytic and non-ionic surfactants and emulsifiers. Examples of suitable surfactants are described in published application 2004/0170670 which is hereby incorporated by reference.

In accordance with another aspect of the present invention, and in consideration of the applications or end uses to be made of the resulting shaped polyurethane foam products, a wide range of other polymers or pre-polymers may be incorporated into the aqueous phase prior to its mixture with the separate pre-polymer mix in a mix head for casting.

Hydrogel materials are useful for certain personal care applications. PECOGEL® H-12 AND GC 310, dimethylaminoethylmethacrylate/polycarbamyl polyglycol esters are useful for hair conditioning and styling applications. PECOGEL H-115, polycarbamyl polyglycol esters and PECOGEL 1220 are for similar hair applications but have greater water resistance. Other hydrogels include dimethiconylacrylate/polycarbamyl polyglycol esters. These polymers are also available as part of the AQUAMERE™ H,A,C and S series as cosmetic hydrogel ingredients. Polyvinyl stearyl ethers, isododecane acrylates and copolymers, acrylic resin, TEA salt, and poly 2-acrylamido-2-methyl propane sulfonic acids such as are available under the trade name GIOVAREZ® are also useful for incorporation in the aqueous phase. Additionally useful polymers for the aqueous phase include monoalkyl esters of polymethyl vinyl ether/maleic acid polymers, quarternized copolymers of vinylpyrrolidone and dimethylaminoethyl methacrylate, vinylpyrrolidone/vinyl acetate copolymers, alkylated vinylpyrrolidone polymers, polyvinyl pyrrolidone, polyethylene glycols, polyacrylate copolymers, and mixtures thereof.

Silicones and polymers of a wide variety are also useful for incorporation into the aqueous phase for certain applications. Dow Corning 193 Fluid which is PEG 12 Dimethicone, Dow Corning 1418 Fluid which is polydimethylsiloxane, Dow Corning Fluid 344 which contains cyclotetrasiloxane and cyclopentasiloxane are examples of useful components for selected applications.

In another embodiment of the present invention, it is preferred to incorporate in the aqueous phase from about 0.1 to about 10 percent by weight of a relatively low molecular weight PEO especially when the resulting layered integrated foam shape is designed for use as a comfort strip. Incorporation in the aqueous phase results in incorporation of minor amounts of the PEO dispersed in the urethane layers in addition to the PEO or other working ingredient distributed and contained in the core region.

In a more preferred embodiment the present invention is carried out according to the following steps:

a) casting onto a surface an aqueous reaction mixture containing a urethane pre-polymer and, optionally, containing a dimensional control ingredient in a ratio effective to produce a dimensionally stable foam of the desired stiffness or softness when cured; releasably covering the cast material and passing it through a compression zone to produce a first layer of uncured polyurethane foam;

b) removing the releasable covering from said first layer;

c) distributing a composition containing a working ingredient that is an absorbent or that releases over time when exposed to a solvent onto said first layer of uncured polyurethane;

d) thereafter adding a second layer of uncured polyurethane on said first layer to produce an uncured layered mass containing a core region enriched in said working ingredient, e) releasably covering said uncured layered mass, passing same through a compression zone, and curing to produce a cured, dimensionally stable layered integrated shaped hydrophilic polyurethane foam.

In a preferred embodiment, the process of the present invention is carried out by casting the pre-polymer mix onto a moving surface or belt, most preferably covered with a release paper or like material and carrying out steps "a" through "e", above, serially on the moving surface.

In accordance with the present invention it is an important advantage from a process standpoint in relation to prior processes that the pre-polymer and aqueous phases can be formulated independently of each other before they are mixed for casting and curing. Adding the working ingredients such as PEO downstream directly to the uncured polymer instead of in the pre-polymer phase is an important advantage. We have found that only limited amount of working ingredient such as PEO can be added in the pre-polymer phase due to viscosity constraints. In accordance with this invention, higher levels of working ingredients including PEO, PEO encapsulates, and other anhydrous slip agents can be distributed and layered more effectively into the core region between the same or different foam layers.

In accordance with the present invention it is further advantageous that all fluid forms of working ingredients can be distributed onto and contained in the core region. Known methods do not enable the use of liquids or suspensions in the final shaped foam product yet this is readily accomplished in accordance with the present invention.

In accordance with another aspect of the present invention, where it is desirable to produce a shaped polyurethane product where the foams of both layers are essentially the same, this can be achieved by adjusting the properties of the releasable material employed for covering the first cast layer, such as release paper, by techniques known to those skilled in the art such that a substantial fraction, e.g. about 25-75% of the first layer is adhered to the release paper as it passes out of the compression zone and is lifted off the first uncured layer to permit adding the working ingredient. Depending on the surface treatment and properties of the release paper and the degree of compression a lesser or greater fraction of uncured polyurethane may be adhered to it. After distributing the working ingredient such as PEO on the remaining first layer, the release paper containing the adhered and still uncured fraction is applied downstream as the second uncured layer and then compressed and cured to form the layered integrated and shaped mass containing a core region enriched in the working ingredient.

It is a highly advantageous alternative aspect of the process of the present invention, that where it is desirable to produce layers of polyurethane foam having different properties such as one layer having a relatively open pore structure for absorbing or desorbing working ingredient contained in the core region, and a second layer having a fine or relatively impervious pore structure, the two layers can be cast efficiently from separate mixing heads where different pre-polymer and aqueous phases can be brought together around the working ingredient core layer to produce the layered integrated foam shape comprising two different layers with the desired properties.

One preferred application of the shaped foam product of the present invention is to make comfort strips which are skin engaging members employed in safety razors for wet shaving. The dimensionally stable layered integrated shaped product, made by the methods of the present invention, may be further cut into shapes and sizes for insertion as the skin engaging member. Alternatively, depending on the working ingredient incorporated by the process of the present invention, the final product is cut or sized for use in other applications as described herein.

The method of incorporating PEO and other water soluble polymers results in advantageous comfort strips that may be used over and over again with successive wettings and drying as a result of the high loading and extended release properties of the layered integrated shaped product where the inner region is enriched in a water soluble polymer.

DETAILED DESCRIPTION OF THE INVENTION

Figure 1:
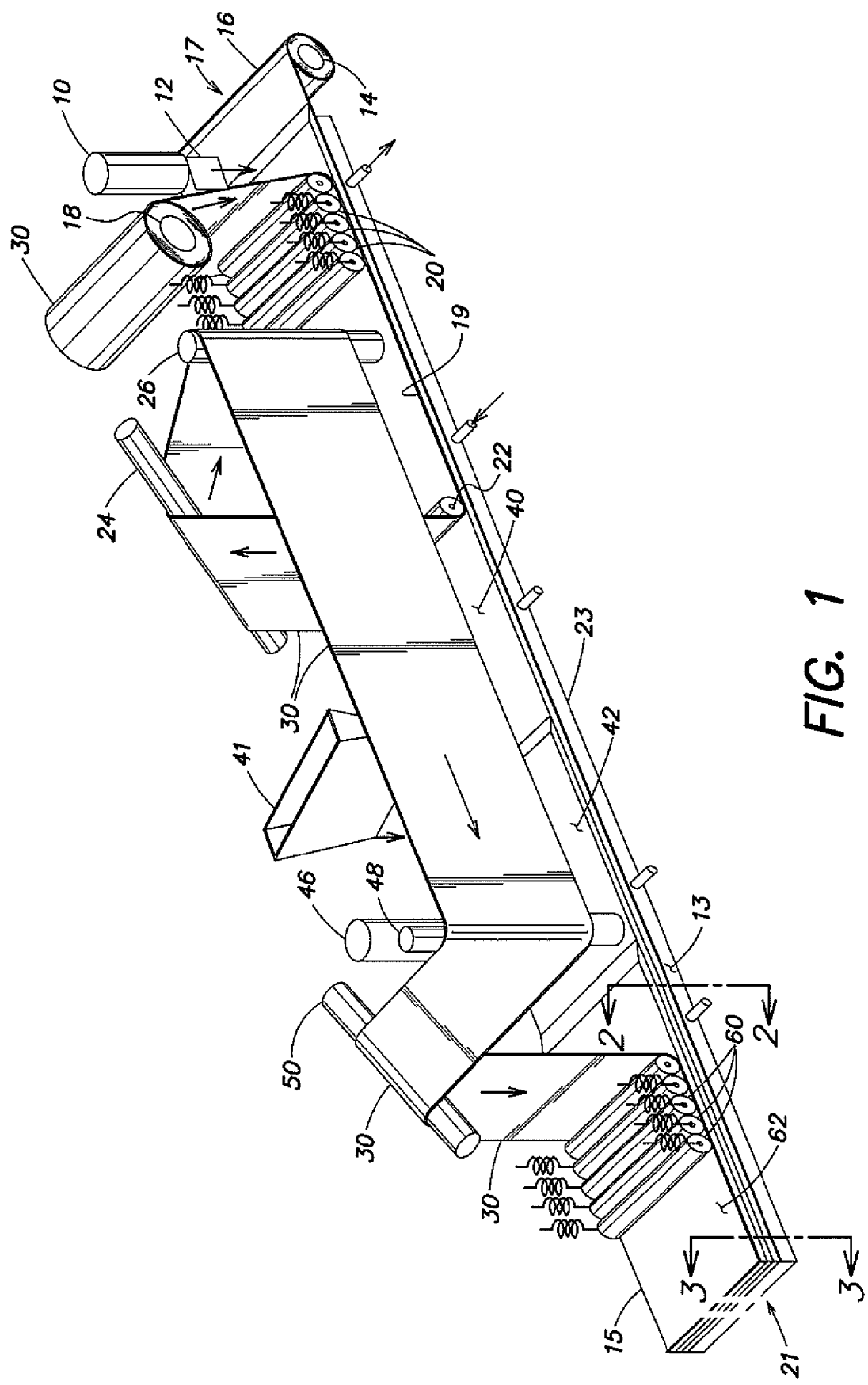
FIG. 1 depicts a system for preparing layered integrated shapes of polyurethane containing pre-measured amounts of working ingredient such PEO.

In the course of development of the concepts of the present invention, we have found that for the preparation of dimensionally stable products such as comfort strips for razor use, the amount of PEO that can be incorporated in a pre-polymer mixture is limited by viscosity and related considerations; and, accordingly, pre-incorporation of PEO in pre-polymer mixtures of hydrophilic polyurethanes does not result in adequate loading of PEO in the foam. Using known procedures, we have found that PEO may be incorporated up to about 25 percent by weight of the aqueous pre-polymer mixture but not above due to viscosity considerations that defeat efficient mix head operation. In addition, we have found that the addition of PEO and the like to such aqueous pre-polymer mixtures limits the use some of the commercially available pre-polymers which are desirable to produce a wide range of useful foam or sponge products for a variety of applications.

We have also determined in development of the concepts of the present invention, that post-addition of PEO and the like to hydrophilic polyurethane foams does not result in completely satisfactory loading of PEO to achieve extended life as needed for advanced comfort strips for safety razors.

In accordance with the methods of the present invention, we have overcome a variety of problems to provide new and useful products of the processes. Accordingly, layered integrated and dimensionally stable hydrophilic polyurethane foams containing a central region or layer enriched in a pre-measured amount of water soluble polymer such as PEO are produced by the present process which are useful for many wetting and drying cycles such as occur in the repeated daily use of wet shaving razors containing comfort strips. PEO is released over an extended period of time from the core region as it is wetted and then dried during use over an extended period of days. Comfort strips made from the product of the process of this invention provide desirable extended release of PEO and other working ingredients and are advantageous over the prior art.

It is known to incorporate vitamins and soothing ingredients such as aloe in comfort strips of the prior art. These and other like ingredients may be distributed together with PEO and the like by the methods of the present invention.

In accordance with the present invention, layered integrated shapes of dimensionally stable hydrophilic polyurethane foams are produced comprising outside layers of the desired urethane foam and an internal region or layer enriched in a suitable working ingredient including water soluble polymers such as polyethylene oxide (PEO).

This is accomplished by casting an aqueous hydrophilic polyurethane pre-polymer reaction mixture onto a surface preferably covered with a release paper, covering the cast mixture with a second release paper and passing the release paper protected mass through compression rollers to produce a first uncured polymer layer of the desired thickness and width. While still uncured, a portion of the top or second release paper is deflected or removed to permit distributing a composition comprising a pre-measured amount of a working ingredient such as PEO, for example, onto the first uncured urethane layer. A working ingredient such as PEO may be added to the uncured urethane layer either as a finely divided solid or in fluid form by equipment known in the art. Following addition of the PEO and before replacing the release paper, a second pre-polymer reaction mixture is cast on top of the PEO containing first uncured urethane layer. Release paper is then placed or replaced on top of the resulting layered mass and passed through compression rollers to produce a an integrated, layered polyurethane foam product of the desired thickness containing a central core enriched in PEO. The resulting product after curing may be further shaped by cutting into the desired size and shape for applications such as comfort strips useful as shaving aids in safety razors.

We have found in accordance with the methods of the present invention, that relatively high percentages of PEO may be incorporated into the central region of the integrated and layered hydrophilic polyurethane. The precise amounts of water soluble polymer such as PEO that are needed depend on the specific application and desired product quality to be achieved. In the preparation of comfort strips or shaving aids for use in safety razors any suitable amount of water soluble polymer such as PEO may be incorporated. Preferred amounts of water soluble polymer are between about 20 and about 80 percent, and most preferred amounts are between about 30 and about 50 weight percent of the weight of the final layered shaped polyurethane foam product. These ranges also apply to other working ingredients as described herein Referring to FIG. 1, an aqueous phase and a separate pre-polymer phase are introduced into mixing zone 10. Examples of compositions for use in making dimensionally stable hydrophilic polyurethane foams in accordance with the methods of the present invention are described in Examples 1 thru 5 below.

Although employing PEO or other water soluble polymers in the pre-polymer reaction mixtures for additional loading as needed is within the present invention, it is preferred to employ reaction mixtures which do not contain PEO or the like to avoid viscosity and related problems. However, employing small amounts of PEO at low levels where viscosity or other problems are minimized in the pre-polymer mix for making either one or both of the polyurethane shapes is within the scope of the present invention. Accordingly, PEO or other water soluble polymers as described herein are added in weight percent amounts from about 0.1 to about 10 percent.

An aqueous pre-polymer mix is passed through mix head 12 and cast onto bottom release paper 16 from roller 14. In this example the release paper and the mix cast onto it is moving at a controlled rate from the upstream process end 17 toward the downstream process end 21. Any suitable mixing and dispensing equipment may be employed to cast the aqueous pre-polymer mix onto the release paper. It is desirable to cast sufficient amounts of the pre-polymer to fully cover the bottom release paper from side 15 to side 13 as depicted in FIG. 1. The bottom release paper is supported on base 23 which may be heated by known means such as the hot water pipes shown to control the viscosity and curing rate of the polyurethane as it is moves forward from end 17 toward 21 of FIG. 1. Suitable commercial mixing and dispensing equipment for polyurethane are known in the art for example, from ESCO, an Edge Sweets Company.

The urethane pre-polymer cast on release paper 16 is passed through a compression zone depicted in FIG. 1 as compression rollers 20. The compression rollers may be spring mounted to provide a way of adjusting the tension and for making a first urethane layer 19 of the desired thickness depending on the end use for which the product is designed. Any suitable method and means for adjusting the dimensions and surface conditions of the uncured polyurethane foam may be employed. Prior to passage through compression rollers 20, top release paper 30 dispensed from roller 18 and is fed such that it passes below compression rollers 20 to prevent the first uncured urethane layer from adhering to the rollers and to assure a more uniform layer of partially cured urethane foam.

The degree of curing of first partially cured or uncured urethane foam layer 19 before distributing thereon a working ingredient such as PEO depends on the speed of movement of the foam layer on the release paper and the temperature of the heated base 23. The speed of movement is adjusted so that the uncured foam reaches distributor means 41, preferably, in less than about 30 seconds and most preferably in less than 10 seconds. If necessary control means not shown in the figure are employed to apply pressure to the release paper before it is picked up at roller 22 to prevent uncured layer 19 from rising due to continued reaction. Similar control means may be required as the layered integrated mass exits rollers 60.

If the interval before adding a working ingredient such as PEO is too long, the urethane polymer cures to such an extent that the PEO can no longer be satisfactorily integrated into the first urethane polymer and the polymer no longer integrates with the second polyurethane layer and the working ingredient to provide an integrated layered mass. Since the cured polyurethane comprises a matrix of open pores, a portion of the liquid or particulate PEO may be lost where the urethane layer is fully or mostly cured before addition of the PEO.

Release paper 30 is lifted off the uncured foam at roller 22 exposing uncured or partially cured urethane surface 40 to enable distributing a working ingredient such as PEO and to enable depositing the second layer of uncured polyurethane over the distributed working ingredient. The conditions including the composition of the release material, additives sprayed on the release paper, temperature, and pressure of the compression rollers 20 can be adjusted by techniques known in the art to cause preferably from about 25 to about 75 percent of uncured foam layer 19 to adhere to the release material leaving behind the remainder to be moved forward to distributor 41. Alternatively, the conditions of the release material and other factors described above can be adjusted such that essentially no uncured urethane foam is adhered to release paper 30 as it lifts off at roller 22. Uncured foam lifted off at roller 22 on release paper 30 is recombined as the top layer or a portion of the top layer as release paper 30 passes under the second set of compression rollers 60.

A working ingredient such as PEO or other suitable water soluble polymer is distributed onto uncured polyurethane foam surface 40 at distributor zone 41. Means known in the art for measuring and distributing powdered or particulate PEO and the like are employed to add a pre-measured amount of PEO evenly across the full width of the uncured foam. Equipment for distributing measured amounts of particulate materials is known from Gough Econ, Inc. of Charlotte, N.C., such as their linear vibratory feeder Model GF. K-Tron provides a series of feeders for accurately distributing pre-measured volumes of particulates having a constant bulk density. Likewise, PEO and other working ingredients can be added in fluid form as a partly solubilized aqueous suspension or fully dissolved solution by liquid dispensing or spraying means known in the art. For example, The Dubois Equipment Company's SP-12 spray unit is suitable for distributing pre-measured amounts of working ingredients in liquid and other fluid forms according to the present invention.

While the invention is described with reference to distributing the working ingredient such as PEO on top of a first or single layer of uncured foam, distributing the working ingredient equally or in any desired proportions on two or more layers of uncured foam prior to combining the layers to make the layered integrated shape having at least one core layer enriched in the working ingredient is within the scope of this invention. Employing this invention to make a plurality of foam layers each containing a core region of working ingredient is also within the scope of this invention.

In the preparation of dimensionally stable hydrophilic polyurethane foams containing a core layer of PEO for purposes of making comfort strips the thicknesses of the entire layered integrated shaped foam are preferably from about 2 to about 10 mm. For many applications greater thicknesses from a few millimeters to a centimeter are desirable. However, depending on the application and equipment employed shaped foam products of any desired dimensions can be produced according to the present invention The temperature of base 23 is controlled by suitable heating means known in the art including the hot water pipes shown in FIG. 1. Other known means include electrical resistance means, convection heating means whereby hot air contacts the curing polymers, and means employing radiant and actinic light. The temperature is controlled so as to effect the desired curing rate of the polymers.

Referring to release paper 30 which is lifted off of the first uncured polyurethane foam layer 19, in the embodiment shown in FIG. 1, additional rollers 24, 26, 48 and 50 are deployed so as to deflect or lift off the release paper 30 beyond the point of second mixing zone 46 where it is then replaced. The configuration shown in FIG. 1 preserves uncured foam that adheres to the release paper such that it remains intact for recombination under compression rollers 60.

Figure 2:
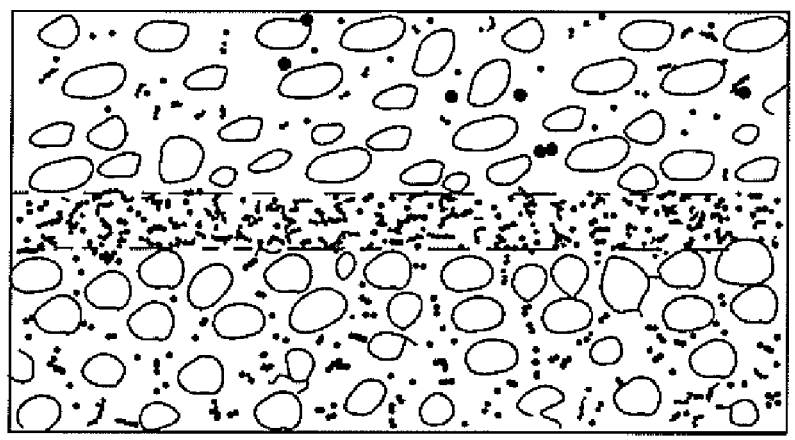
FIG. 2 is a cross-section taken at the point shown by the numerals 2 and the arrows depicting an upper and lower polyurethane foam layer each with pores and a central core region containing a powdered working ingredient such as PEO prior to final compression of the layers.
Figure 3:
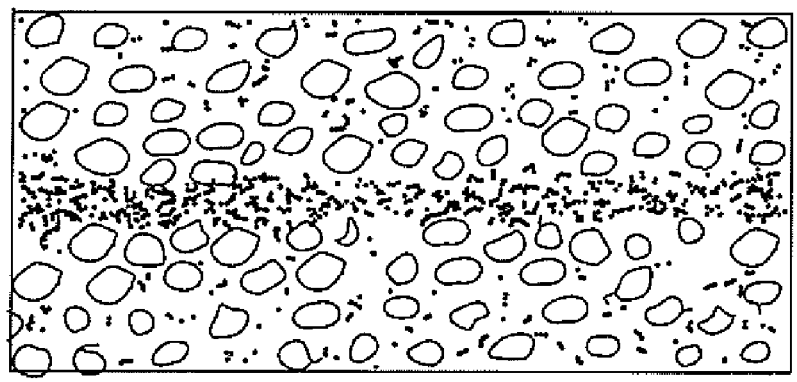
FIG. 3 is a cross-section taken at the point shown by the numerals 3 and the arrows depicting an upper and lower polyurethane foam layer each with pores and a central core region containing a powdered working ingredient such as PEO after final compression of the layers.
Figure 4:
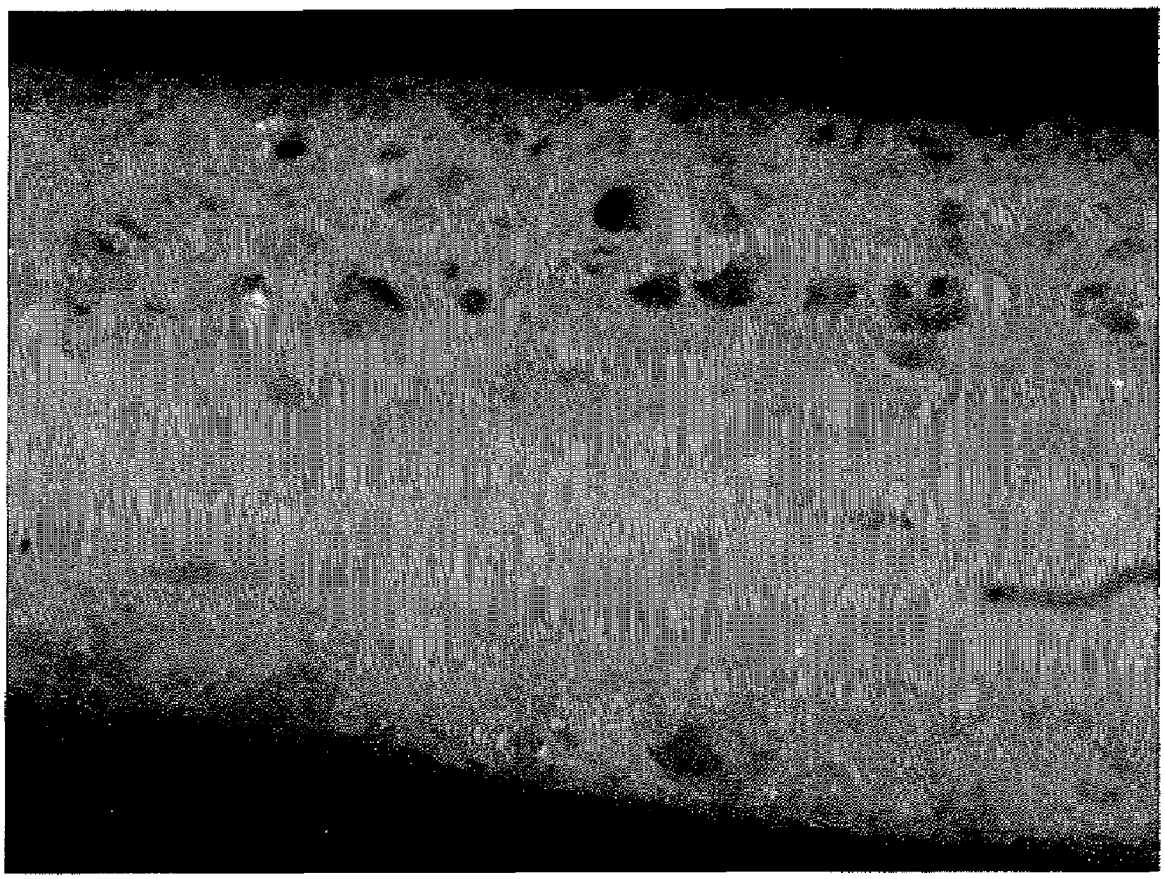
FIG. 4 is a photomicrograph of the product of the process described with reference to FIG. 1 below.

A second aqueous pre-polymer mix is introduced into second mixing zone 46. The aqueous pre-polymer mixture is the same or different in composition from the one employed to make the first urethane foam layer. The foam depicted in cross-section in FIGS. 2 and 3 is representative of foam made with pre-polymer mixtures that are the same for both the first and second urethane foam layers.

In FIG. 1, a second urethane foam layer 62 is cast onto the surface of the first layer 19 downstream of the point in the process where a PEO layer 42 is distributed on the first foam layer. The second foam layer is cast from a pre-polymer mixture contained in mixer tank 46 and a mix head hidden from view by the release paper. The second layer preferably covers layer 42 from side 13 to side 15. The mass comprising the first uncured foam layer 19, PEO layer 42 and second uncured foam layer 62 is covered with the release paper 30 and passed through compression rollers 60. Release paper 30 is fed from roller 50 below the compression rollers to protect the surface of the second uncured urethane layer as it passes under rollers 60 thereby permitting a smooth surface to be formed on second urethane layer 62 and to form an integrated, layered urethane foam shape containing a core layer of a working ingredient such as PEO. The foam shape is permitted to cure either under ambient conditions or with heating beyond end 21 of FIG. 1.

The following examples 1 through 5 illustrate producing a layered integrated polyurethane foam product useful for making comfort strips for wet shave razors which contain a core region enriched in PEO. In examples 1-5, PEO-2 is purified PEO from Rita Chemical Co. having a molecular weight about 400,000. The ingredients listed as PEO is a PEO powder from Dow Chemical Company and that powder is distributed onto the uncured foam. Pluronic L-44 is a non-ionic surfactant, polyoxyethylene-polyoxypropylene block co-polymer. The aqueous phase is made up of PEO-2, Pluronic L-44, Wollastonite 400 and water. Hypol JM-5002 is a hydrophilic polyurethane pre-polymer, methlylenediphenyl diisocyanate.

EXAMPLE 1

| Ingredient | formulation weight % | dry shape wt. % |
|---|---|---|
| Distilled water | 21.87 | 4.87 |
| PEO-2 | 1.04 | 1.27 |
| Pluronic L-44 | 3.11 | 3.79 |
| Wollastonite 400 | 26.04 | 31.70 |
| Hypol JM-5002 | 22.32 | 27.18 |
| PEO | 25.62 | 31.19 |
| Total | 100 | 100 |

The PEO from Dow was screened material that passed through 40-mesh screen and was held on 60-mesh; the PEO was 40-mesh.

Aqueous to polymer ratio was 70% aqueous phase to 30% polymer phase.

The layered integrated shape was made in the following manner: a first layer of uncured urethane foam was made by casting the aqueous pre-polymer reaction mixture between two sheets of release paper and molded in a metal box to form a compressed layer or sheet. Then the top release paper was pulled up exposing two halves that were about equal and formed layers. Next the PEO (40 mesh) was distributed evenly on the bottom layer while still uncured prior to replacing the top layer on the bottom layer. The resulting layered mass was then compression molded in a metal box to form a porous hydrophilic foam shape approximately 3 mm thick containing the PEO as a core region or layer. Each step was determined gravimetrically. Total PEO was 32.46%

EXAMPLE 2

| Ingredient | formulation weight % | dry shape wt. % |
|---|---|---|
| Distilled water | 20.59 | 6.33 |
| PEO-2 | 1.00 | 1.58 |
| Pluronic L-44 | 2.94 | 4.65 |
| Wollastonite 400 | 24.51 | 38.80 |
| Hypol JM-5002 | 21.02 | 33.28 |
| PEO | 29.94 | 15.36 |
| Total | 100 | 100 |

The PEO from Dow was screened material that passed through 100-mesh screen and was held in a pan; the PEO was 100-mesh. Aqueous to polymer ratio was 70% aqueous phase to 30% polymer phase. The layered integrated shape was made in the following manner: a first layer of uncured urethane foam was made by casting the aqueous pre-polymer reaction mixture between two sheets of release paper in a metal box to form a compressed layer or sheet. Then the top release paper was pulled up exposing two halves that were about equal and formed layers. Next the PEO (100 mesh) was distributed evenly on the bottom layer while still uncured prior to replacing the top layer on the bottom layer. The resulting layered mass was then compression molded in a metal box to form a porous hydrophilic foam shape approximately 3 mm thick containing the PEO as a core region or layer. Each step was determined gravimetrically. Total PEO was 16.94%.

EXAMPLE 3

| Ingredient | formulation weight % | dry shape wt. % |
|---|---|---|
| Distilled water | 42.51 | 6.51 |
| PEO-2 | 0.69 | 1.12 |
| Pluronic L-44 | 2.04 | 3.32 |
| Wollastonite 400 | 17.07 | 27.76 |
| Hypol JM-5002 | 14.63 | 23.79 |
| PEO | 23.06 | 37.50 |
| Total | 100 | 100 |

The PEO from Dow was screened material that passed through 100-mesh screen and was held in a pan; the PEO was 100-mesh. Aqueous to polymer ratio was 70% aqueous phase to 30% polymer phase. The layered integrated shape was made in the following manner: a first layer of uncured urethane foam was made by casting the aqueous pre-polymer reaction mixture between two sheets of release paper in a metal box to form a compressed layer or sheet. Then the top release paper was pulled up exposing two halves that were about equal and formed layers. Then 6.35 grams of distilled water was sprayed on each half. Next the PEO (100 mesh) was distributed evenly on the bottom layer while still uncured prior to replacing the top layer on the bottom layer. The resulting layered mass was then compression molded in a metal box to form a porous hydrophilic foam shape approximately 3 mm thick containing the PEO as a core region or layer. Each step was determined gravimetrically. Total PEO was 38.62%

EXAMPLE 4

| Ingredient | formulation weight % | dry shape wt. % |
|---|---|---|
| Distilled water | 23.70 | 4.98 |
| PEO-2 | 1.13 | 1.41 |
| Pluronic L-44 | 3.38 | 4.21 |
| Wollastonite 400 | 28.23 | 35.16 |
| Hypol JM-5002 | 24.19 | 30.12 |
| PEO | 19.37 | 24.12 |
| Total | 100 | 100 |

The PEO from Dow was screened material that passed through 40-mesh screen and was held on 60-mesh; the PEO was 40-mesh. Aqueous to polymer ratio was 70% aqueous phase to 30% polymer phase. The layered integrated shape was made in the following manner: two separate aqueous pre-polymer reaction mixtures were cast on release paper and compressed in a metal box to form individual sheets for an upper and lower uncured foam layers. Next the PEO (40 mesh) was distributed evenly on the bottom layer while still uncured and then covering the PEO and bottom layer with the other or top layer. The resulting layered mass was then compression molded in a metal box to form a porous hydrophilic foam shape approximately 3 mm thick containing the PEO as a core region or layer. Each step was determined gravimetrically. Total PEO was 25.53%.

EXAMPLE 5

| Ingredient | formulation weight % | dry shape wt. % |
|---|---|---|
| Distilled water | 19.83 | 3.61 |
| PEO-2 | 0.93 | 1.12 |
| Pluronic L-44 | 2.83 | 3.40 |
| Wollastonite 400 | 23.60 | 28.38 |
| Hypol JM-5002 | 20.23 | 24.32 |
| PEO/CMC 2500 mix | 32.58 | 39.17 |
| Total | 100 | 100 |

The PEO from Dow was screened material that passed through 40-mesh screen and was held on 60-mesh; the PEO was 40-mesh. A 50/50 mix was made using CMC 2500 hydrated powder and the PEO. Aqueous to polymer ratio was 70% aqueous phase to 30% polymer phase. The layered integrated shape was made in the following manner: a first layer of uncured urethane foam was made by casting the aqueous pre-polymer reaction mixture between two sheets of release paper in a metal box to form a compressed layer or sheet. Then the top release paper was pulled up exposing two halves that were about equal and formed layers. Next the PEO/CMC 2500 mix was distributed evenly on the bottom layer while still uncured prior to replacing the top layer on the bottom layer. The resulting layered mass was then compression molded in a metal box to form a porous hydrophilic foam shape approximately 3 mm thick containing the PEO as a core region or layer. Each step was determined gravimetrically. Total PEO was 40.29%

EXAMPLES 6-14

The following examples illustrate employing the integrated layered shaped polyurethane foam containing a core region of selected working ingredients for a wide variety of different applications.

EXAMPLE 6

In this example, a layered integrated polyurethane foam product is produced for use as an absorbent wound dressing that exudes a bioactive working ingredient that aids in the healing process. A working ingredient comprising bioactive powdered glass, hydrogel, polyethylene glycol, PVP (polyvinylpyrollidone) and PVP/vinyl acetate copolymer is distributed onto first uncured layer 19 and then processed to add a second uncured layer by splitting the first layer and then recombining it downstream as described with reference to FIG. 1. The working ingredient that forms the core region of the final foam product is distributed onto the uncured foam preferably from about 5 to about 30% by weight of the total product, and in this example about 15% by weight. The layered integrated foam pad has a thickness of about 3 mm and is employed as a wound dressing where moisture and other bodily fluids are absorbed in the hydrophilic foam while the bioactive ingredient is slowly released. In this example, the ratio of pre-polymer (Hypol 2002) to aqueous phase is 1 to 2.3 thereby providing relatively soft foam. The working ingredient is released over the period of about one-day. An antibiotic working ingredient is incorporated and applied in the same manner as described above.

EXAMPLE 7

In this example, a layered integrated polyurethane foam product is produced for use as a dry cleaning and spot remover sheet. In this example, a water-based gel dry cleaning agent composition containing nonionic surfactant, an amphoteric surfactant, a polysaccharide gelling agent, diethylene glycol monoethyl ether solvent, a metal halide salt and fragrance is distributed onto first uncured layer 19 and then processed to add a second uncured layer by splitting the first layer and then recombining it downstream as described with reference to FIG. 1. The working ingredient that forms the core region of the final foam product is distributed onto the uncured foam preferably from about 5 to about 30% by weight of the total product, and in this example about 15% by weight. The foam pad has a thickness of about 5 mm and is placed in a dryer safe re-closable bag in a home dryer together with a wool sweater to be cleaned and treated for 30 minutes. In this example, the ratio of pre-polymer (Hypol 3000) to aqueous phase is 1 to 2.3 thereby providing relatively soft foam. With the heat and agitation of the dryer, the dry cleaning agent in the core region is released in less than about 30 minutes.

EXAMPLE 8

In this example, a fabric softener formula containing an alkali metal stearate, quaternary amine fabric softening agents, synthetic and natural waxes, fatty alcohol surfactants, other softening ingredients (amides and derivatives), nonionic surfactants, powdered dispersants including talc and wollastonite is incorporated via dispensing zone 41 of FIG. 1 to make a layered integrated product for use by placing in a dryer for release of the formula over a 30 minute drying cycle. A related sheet is made containing anti static agents of silicone surfactants and silicone polymers for use in a home dryer while drying home laundry with minimum static electricity.

EXAMPLE 9

In this example, a layered integrated polyurethane foam product is produced for use as a dual sided foam pad for cleaning pots and pans. In this example, a slow dissolving powdered detergent composition consisting of sodium carbonate, sodium sesquicarbonate, sodium sulfate, anionic surfactant, nonionic surfactant, powdered filler/abrasive (feldspar, pumice) and fragrance is distributed via means 41 onto first layer 19 while uncured to form the core region. In this example 20% by weight of the total product is used, however, preferably from about 5 to about 20% by weight is applied to form the core region. Abrasives can be dispersed in the aqueous phase to be mixed with pre-polymer (Hypol 3000) producing the first and second layer of hydrophilic polyurethane layer.

EXAMPLE 10

In this example, a layered integrated polyurethane foam product is produced for use as a strip of foam for hair treatment as a hair styling mouse for application to wet hair. In this example the following ingredients are distributed on uncured polyurethane layer 19 via dispenser 41: water, anionic surfactant, nonionic surfactant, vinyl caprolactam/VP/dimethylaminoethyl methacrylate copolymer, VP/dimethylaminoethyl-methacrylate copolymer, vinylpyrrolidone/vinyl acetate copolymer, powdered PVP, quaternized copolymer of vinylpyrrolidone and dimethylaminoethyl methacrylate, and amodimethicone (and) cetrimonium chloride (and) trideceth-10. The layer 19 is then processed to add a second uncured layer by splitting the first layer and then recombining it downstream as described with reference to FIG. 1. The working ingredient that forms the core region of the final foam product is distributed onto the uncured foam preferably from about 30 to about 50% by weight of the total product, and in this example about 40% by weight. The foam pad has thickness of about 5 mm and in this example, the ratio of pre-polymer (Hypol 3000) to aqueous phase is 1 to 1 thereby providing relatively soft foam where the mousse-forming ingredient is released in less than 2 minutes. Similar foam pads are made for use in application of hair coloring agents, hair cleansing, shampoo application, for removal of facial hair, and also for application of men's hair growing foam such as Rogaine®.

EXAMPLE 11

In this example, an integrated layered polyurethane foam product is produced for use as a floating oil absorbing sheet where the oil is a hazardous waste spill. In this example granular shreds of hydrophilic polyurethane foam particles consisting of water, feldspar, silicone fluid, mineral spirits, an organo-silane coupling agent, anionic surfactant, nonionic block copolymer surfactant and a hydrophilic polyurethane pre-polymer are processed into an open-celled foam and ground into 8 to 11 mesh particles. These granules are a highly effective absorbent and are distributed onto first layer 19 while uncured. In this application, first layer 19 is selected to produce open celled foam where the ratio of pre-polymer (Hypol 3000) to the aqueous phase is 1 to 9. While second layer 62 is selected to provide a closed cell polyurethane foam using pre-polymer (Trepol T-1) which when cured makes a layered integrated product that floats on water. In this example the thickness of the total foam product is 1 to 2 cm. In this example, the added working agent does not dissolve but rather absorbs oil.

EXAMPLE 12

In this example, a layered integrated polyurethane foam product is produced for use as an anti-spotting aid in a home dishwasher. An anti-spotting formula containing fatty amide, nonionic surfactant, synthetic wax, and solubility control agent is incorporated via dispensing zone 41 and then processed as described above to produce an anti-spotting detergent booster sheet. Preferably about 10 to about 40% by weight of the total product is added as the core layer, and in this example about 25% by weight is used. The thickness of the total foam pad is 3 to 5 mm. The ratio of pre-polymer (Trepol T-1) to aqueous phase is 1 to 1.5 thereby providing relatively stiff yet absorbent foam where the anti-spotting agent is released over time primarily in the rinse cycle.

EXAMPLE 13

In this example, a layered integrated hydrophilic polyurethane foam is made for use as a disinfectant hard surface cleaning sheet. A powdered cleaner-disinfectant formula containing sodium sulfate, sodium carbonate, sodium sesquicarbonate, anionic surfactant, nonionic surfactant, pine oil, quaternary ammonium compound (or phenol) is incorporated via means 41 to make a layered integrated polyurethane foam with the processing described above. Preferably this working ingredient is from about 5% to about 30% by weight of the total product. In this example the thickness of the foam sheet is 3 mm to 5 mm and the ratio of pre-polymer (Trepol T-1) to aqueous phase is 1 to 1. The layered integrated product is relatively firm and the cleaner-disinfectant formula is useful over several applications.

EXAMPLE 14

In this example, relatively soft foam sheets are produced by incorporating a make up removal agent emulsion via dispensing zone 41 with further processing into a layered integrated shaped foam sheet as described above. This working ingredient comprises about 30-65% water, about 35-60% of a liquid mixture of mineral oil and/or a fatty acid ester mixture; and about 2.5-10% of a mixture of a copolymer of ethylene oxide with a polyoxypropylene block having a molecular weight of about 1500-3500 and a $C_8$-$C_{22}$ fatty acid mono ester of a $C_2$-$C_5$ polyol; and an anionic surfactant component comprising a fatty acid alkanol amine salt, in a weight ratio of nonionic surfactant component to anionic surfactant component of about 1.25-1:1. Preferably about 10% to about 30% by weight of this emulsion, working ingredient, is incorporated into foam and in this example about 20% is used.

In accordance with the process of the present invention and its many useful applications, especially for use in cosmetics applications, a wide range of working ingredients can be selected and incorporated into the uncured polyurethane foams by dispensing zone 41. Such working ingredients are selected from the following groups of ingredients:

Natural, if desired, chemically modified, polymers, selected from among the following: cellulose ethers, quaternized cellulose derivatives, polyquarternium 24, guar gum, cationic guar derivatives, alginates, xanthan gum, gum arabic, karaya gum, carob bean flour, linseed gums, dextrans, shellac, amylose, amylopectin, dextrins, chemically and/or thermally modified starches, and chitosan and its derivatives;

Synthetic polymers that do not act as super absorbers but rather swell with water and are thereby converted to a gel-like true or colloidal solution and this includes materials like PEO;

O-hydroxycarboxylic acids and their derivatives;

Vitamins, provitamins, and vitamin intermediates of the groups B, C, and H and their derivatives;

Plant extracts, selected from among plant formative tissues that are capable of dividing (meristem), green tea (*Camellia sinensis*), hamamelis, chamomile, marigold, pansy, peony, horse chestnut, sage, willow bark, cinnamon tree, chrysanthemums, oak bark, nettle, hops, lappa, horsetail, hawthorn, linden flowers, almonds, spruce needles, sandalwood, juniper, coconut, kiwi, guava, lime, mango, apricot, wheat, melon, orange, grapefruit, avocado, rosemary, birch, beech sprouts, mallow, cuckoo flower, yarrow, wild thyme, thyme, balm mint, resthallow, marsh mallow (Althaea), common mallow (*Malva sylvestris*), violet, leaves of the black currant, coltsfoot, cinquefoil, ginseng, ginger root, sweet potato, olives (*Olea europaea*), and citrus fruit seeds;

Extracts of algae and microorganisms;

Active substances with antiperspirant activity, selected from among astringent water-soluble inorganic and organic aluminum, zinc, and zirconium salts and their mixtures;

Active substances with deodorant activity;

Silicic acids, natural and synthetic silicates, aluminosilicates, kaolin, talc, and apatites, which may be modified with aqueous carboxylic acids with 2-3 C atoms;

Pigments selected from among the oxides of titanium, iron, zinc, zirconium, cerium, magnesium, and bismuth, which, if desired, may be surface-modified, boron nitride particles, water-insoluble nacreous pigments, and water-insoluble organic pigments;

Water-soluble and oil-soluble organic sun screening ingredients;

Cosmetic abrasives selected from among polymer particles and vegetable abrasives, which, if desired, may be coated with fatty substances. XIII. dyes and oxidation dye (intermediates) for dyeing keratinous fibers;

Oxidizing and reducing ingredients, and;

Active substances with sebum-regulating, skin-soothing, anti-inflammatory, astringent, or perfusion-promoting activity.

Many modifications and alterations of the present invention will become apparent from the above description without departing from the scope of the invention.

What is claimed is:

1. A method of making layered integrated shaped product containing dimensionally stable hydrophilic polyurethane foam which comprises: a) casting onto a surface an aqueous reaction mixture containing a urethane pre-polymer containing free isocyanate groups and, optionally, a dimensional control ingredient in a ratio effective to produce a dimensionally stable foam of desired firmness when cured thereby producing a first layer of uncured polyurethane foam and compressing said first layer; b) distributing a composition containing an absorbent or a working ingredient that releases over time when exposed to a solvent fluid onto said first layer of uncured polyurethane; c) thereafter further adding a second layer of uncured polyurethane on said first layer and compressing the resulting uncured layered mass, d) curing the layered mass to produce a resulting layered integrated shaped product of dimensionally stable hydrophilic polyurethane foam containing a core region enriched in an absorbent or a working ingredient that releases over time when exposed to a solvent fluid; wherein said composition contains a working ingredient comprising a water soluble polymer selected from the group consisting of polyethylene oxide, polyvinyl pyrrolidone, polyacrylamide, hydroxypropyl cellulose, polyvinyl imidazoline, and polyhydroxyethylmethacrylate, and co-polymers and mixtures of said polymers; and said composition containing a water soluble polymer is in the form of a powder having a particle size between about 10 and about 300 mesh.

2. The method of claim 1 wherein said composition containing a water soluble polymer is added in a pre-measured amount.

3. The method of claim 1 wherein said aqueous reaction mixture contains a hydrophilic urethane pre-polymer and a dimensional control agent in a ratio capable of producing a dimensionally stable foam when cured.

4. The method of claim 3 wherein said aqueous reaction mixture additionally contains a surfactant.

5. The method of claim 3 wherein the ratio of said prepolymer and dimensional control agent is from about 1:2 to about 2:1.

6. The method of claim 2, wherein the amount of water soluble polymer is between about 20 percent to about 80 percent by weight to the final layerd integrated product after curing.

7. The method of claim 1 wherein said aqueous reaction mixture cast on said surface additionally contains from about 0.01 to about 10 percent by weight of PEO.

8. The method of claim 1, wherein said working ingredient is selected from a composition comprising a bioactive agent or antibiotic for release from the core layer of a bandage or wound dressing foam, a cosmetic ingredient for release from the core layer of a personal care sponge, a detergent or an abrasive for release from the core layer of a cleaning or polishing sponge, a dry cleaning or anti-static agent for release from a sheet for use in a clothes dryer, and an absorbent to take up fluids through the pores of a waste cleanup sponge.

* * * * *